United States Patent
Woo et al.

(10) Patent No.: US 10,709,420 B2
(45) Date of Patent: Jul. 14, 2020

(54) ULTRASONIC IMAGING DEVICE AND MOVING UNIT APPLIED TO THE SAME

(71) Applicant: SAMSUNG MEDISON CO., LTD., Hongcheon-gun, Gangwon-do (KR)

(72) Inventors: Kyeong Gu Woo, Suwon-si (KR); Yeon-Ho Kim, Seongnam-si (KR); Jae Moon Jo, Seongnam-si (KR); Gil-Ju Jin, Seoul (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 1018 days.

(21) Appl. No.: 15/050,174

(22) Filed: Feb. 22, 2016

(65) Prior Publication Data
US 2016/0345935 A1    Dec. 1, 2016

(30) Foreign Application Priority Data
May 29, 2015 (KR) ........................ 10-2015-0075982

(51) Int. Cl.
*A61B 8/00* (2006.01)

(52) U.S. Cl.
CPC ............ *A61B 8/462* (2013.01); *A61B 8/4405* (2013.01); *A61B 8/4444* (2013.01); *A61B 8/467* (2013.01); *A61B 8/464* (2013.01)

(58) Field of Classification Search
None
See application file for complete search history.

(56) References Cited

U.S. PATENT DOCUMENTS

| | | | |
|---|---|---|---|
| 5,924,988 A | 7/1999 | Burris et al. | |
| 6,669,639 B1 | 12/2003 | Miller et al. | |
| 2004/0179332 A1* | 9/2004 | Smith ...................... | A61B 8/00 361/679.41 |

(Continued)

FOREIGN PATENT DOCUMENTS

| | | |
|---|---|---|
| DE | 202005009471 U1 | 10/2005 |
| DE | 202015003181 U1 | 5/2015 |

(Continued)

OTHER PUBLICATIONS

Extended European Search Report dated Oct. 31, 2016 issued in European Patent Application No. 15184674.8.

(Continued)

*Primary Examiner* — Katherine L Fernandez
(74) *Attorney, Agent, or Firm* — Morgan, Lewis & Bockius LLP

(57) ABSTRACT

Disclosed herein is an ultrasonic imaging apparatus including: a main body; a probe; a display unit connected to the main body in such a manner to be movable with respect to the main body; and a moving unit configured to connect the display unit to the main body, and to enable the display unit to move with respect to the main body, wherein the moving unit includes: a first coupling member rotatably attached on a part of the main body; a rotating arm coupled with the first coupling member and configured to rotate with respect to the first coupling member; and a moving member having one end coupled with the display unit, and installed in the rotating arm to enable the display unit to move in a longitudinal direction of the rotating arm.

4 Claims, 15 Drawing Sheets

(56) References Cited

U.S. PATENT DOCUMENTS

| | | | | |
|---|---|---|---|---|
| 2007/0058329 A1* | 3/2007 | Ledbetter | ............... | F16M 11/10 |
| | | | | 361/679.06 |
| 2009/0062657 A1* | 3/2009 | Yanagihara | .............. | A61B 8/00 |
| | | | | 600/459 |
| 2010/0094130 A1* | 4/2010 | Ninomiya | ................ | A61B 8/00 |
| | | | | 600/437 |
| 2012/0182709 A1* | 7/2012 | Asai | .................... | A61B 8/4405 |
| | | | | 361/810 |
| 2013/0030301 A1* | 1/2013 | Nakajima | ............ | A61B 8/4405 |
| | | | | 600/459 |
| 2013/0197364 A1* | 8/2013 | Han | ..................... | A61B 8/4405 |
| | | | | 600/440 |
| 2015/0351719 A1* | 12/2015 | Ninomiya | ............ | A61B 8/4405 |
| | | | | 348/163 |
| 2016/0120507 A1* | 5/2016 | Ninomiya | ............ | A61B 8/4405 |
| | | | | 345/1.3 |

FOREIGN PATENT DOCUMENTS

| | | |
|---|---|---|
| JP | 2008-036283 A | 2/2008 |
| JP | 2010-269068 A | 12/2010 |
| WO | 2014/192815 A1 | 12/2014 |

OTHER PUBLICATIONS

European Communication dated Apr. 15, 2020 issued in European Patent Application No. 15184674.8.

\* cited by examiner

ULTRASONIC IMAGING DEVICE AND MOVING UNIT APPLIED TO THE SAME

CROSS-REFERENCE TO RELATED APPLICATION

This application claims the benefit of Korean Patent Application No. 10-2015-0075982, filed on May 29, 2015 in the Korean Intellectual Property Office, the disclosure of which is incorporated herein by reference.

BACKGROUND

1. Field

Embodiments of the present disclosure relate to an ultrasonic imaging apparatus with an improved structure for easily moving a display unit.

2. Description of the Related Art

An ultrasonic imaging apparatus emits ultrasonic signals toward a target part of a subject from the skin surface of the subject, and receives ultrasonic signals (that is, ultrasonic echo signals) reflected from the target part of the subject so as to non-invasively acquire slice images about soft tissue or images about blood vessels based on information about the ultrasonic echo signals.

The ultrasonic imaging apparatus has advantages that it is a compact, low-priced apparatus and it can display images in real time, compared to other imaging apparatuses, such as an X-ray diagnostic apparatus, an X-ray Computerized Tomography (CT) scanner, a Magnetic Resonance Image (MRI) apparatus, and a nuclear medical diagnostic apparatus. Also, the ultrasonic imaging apparatus has high safety since there is no risk for patients to be exposed to radiation. For the advantages, the ultrasonic diagnostic apparatus is widely used to diagnose the heart, abdomen, urinary organs, uterus, etc.

SUMMARY

Therefore, it is an aspect of the present disclosure to provide an ultrasonic imaging apparatus with an improved structure for easily moving a display unit spaced from a main body.

Additional aspects of the disclosure will be set forth in part in the description which follows and, in part, will be obvious from the description, or may be learned by practice of the disclosure.

In accordance with one aspect of the present disclosure, there is provided an ultrasonic imaging apparatus including: a main body; a probe configured to irradiate ultrasonic waves and to receive ultrasonic waves, and connected to the main body to transmit an ultrasonic signal corresponding to the received ultrasonic waves to the main body; a display unit connected to the main body in such a manner to be movable with respect to the main body; and a moving unit configured to connect the display unit to the main body, and to enable the display unit to move with respect to the main body, wherein the moving unit includes: a first coupling member rotatably attached on a part of the main body; a rotating arm coupled with the first coupling member and configured to rotate with respect to the first coupling member; and a moving member having one end coupled with the display unit, and installed in the rotating arm to enable the display unit to move in a longitudinal direction of the rotating arm.

The moving unit may further include a rack gear and a pinion gear, and one of the rack gear and the pinion gear may move back and forth in the longitudinal direction of the rotating arm.

The first coupling unit may be configured to be rotatable on a first plane, and the rotating arm may be configured to rotate together with the first coupling member.

The rotating arm may be configured to be rotatable on a second plane that is vertical to the first plane.

The display unit may be rotatably coupled with a second coupling member disposed at one end of the moving member.

The moving unit may further include a belt member configured to move in both directions along the longitudinal direction of the rotating arm, and a second coupling member coupled with a part of the belt member and configured to move together with the belt member, and the second coupling member may be coupled with the display unit.

The display unit may be rotatably coupled with the second coupling member.

The moving unit may further include a hydraulic cylinder configured to move back and forth along the longitudinal direction of the rotating arm, and a second coupling member coupled with one end of the hydraulic cylinder and configured to move together with the hydraulic cylinder, and the second coupling member may be coupled with the display unit.

The display unit may be rotatably coupled with the second coupling member.

In accordance with another aspect of the present disclosure, there is provided a moving unit which supports a display unit spaced from a main body and moves the display unit, the moving unit including: a first coupling member attached on a part of the main body, and configured to rotate with respect to the main body; a rotating arm having one end coupled with the first coupling member, and configured to rotate with respect to the first coupling member; and a moving member having one end coupled with the display unit, and installed in the rotating arm to enable the display unit to slide along the rotating arm.

The moving unit may further include a rack gear and a pinion gear, and one of the rack gear and the pinion gear may move back and forth along a longitudinal direction of the rotating arm.

The moving unit may further include a second coupling member coupled with the display unit, at one of the rack gear and the pinion gear, which moves along the longitudinal direction of the rotating arm.

The moving unit may include a hydraulic cylinder configured to move back and forth along a longitudinal direction of the rotating arm, and a second coupling member coupled with one end of the hydraulic cylinder and configured to move together with the hydraulic cylinder, and the second coupling member may be coupled with the display unit.

The moving unit may include a belt member configured to move in both directions along a longitudinal direction of the rotating arm, and a second coupling member coupled with a part of the belt member and configured to move together with the belt member, and the second coupling member may be coupled with the display unit.

The display unit may be configured to rotate with respect to the second coupling member.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
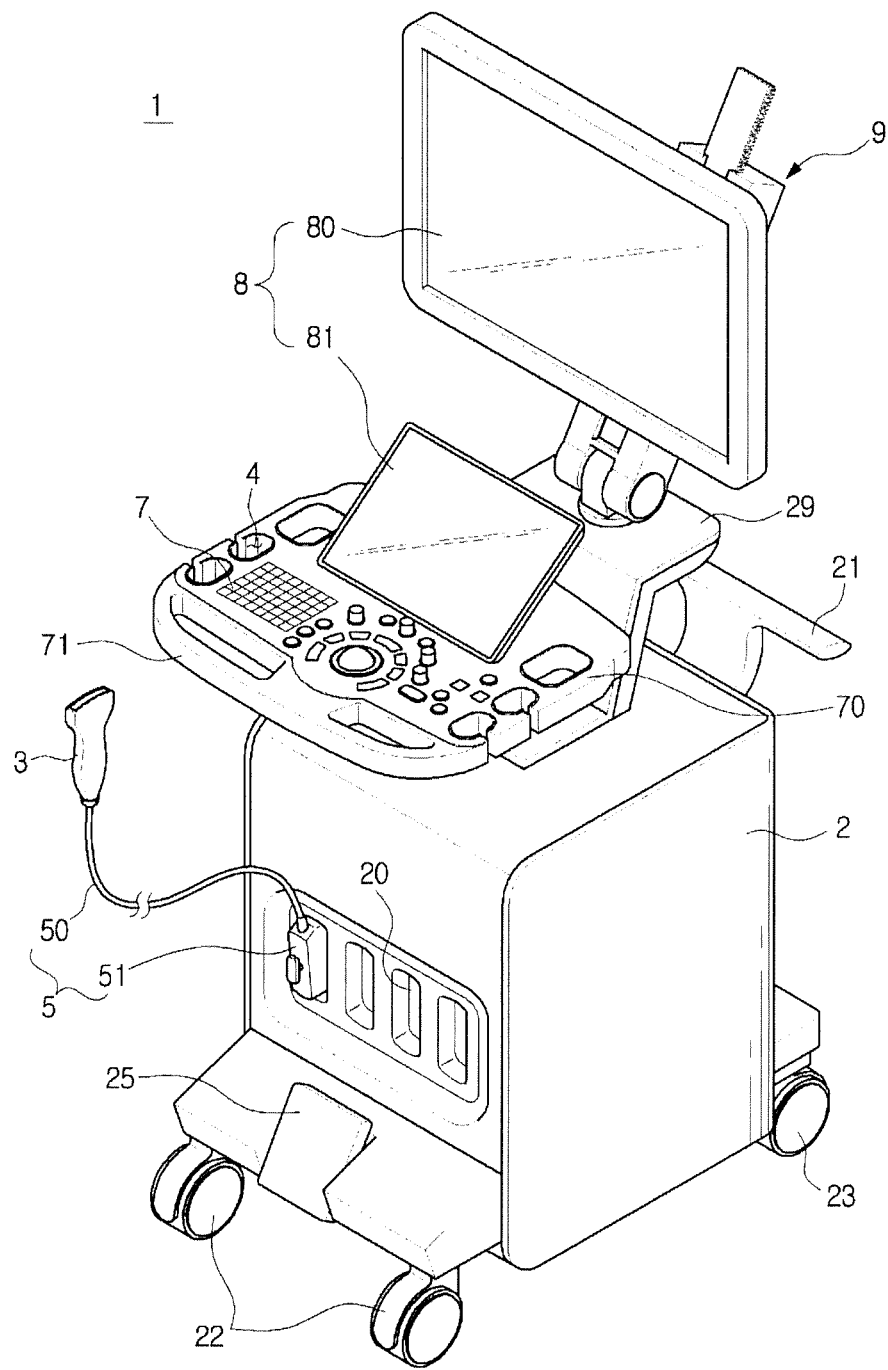
FIG. 1 is a perspective view showing an ultrasonic imaging apparatus according to an embodiment of the present disclosure.

Reference will now be made in detail to the embodiments of the present disclosure, examples of which are illustrated in the accompanying drawings, wherein like reference numerals refer to like elements throughout.

Hereinafter, an ultrasonic imaging apparatus according to an embodiment of the present disclosure will be described in detail with reference to the accompanying drawings.

FIG. 1 is a perspective view showing an ultrasonic imaging apparatus according to an embodiment of the present disclosure.

Referring to FIG. 1, an ultrasonic imaging apparatus according to an embodiment of the present disclosure may include a main body 2, an ultrasound probe 3, an input unit 7, and a display unit 8. The display unit 8 may include a main display 80 and a sub display 81.

The display unit 8 may display ultrasound images acquired during ultrasonic diagnosis. Also, the display unit 8 may display an application related to operations of the ultrasonic imaging apparatus 1. For example, the main display 80 may display ultrasound images acquired during ultrasonic diagnosis, and the sub display 81 may display data related to operations of the ultrasonic imaging apparatus 1.

The main display 80 or the sub display 81 may be implemented as Cathode Ray Tube (CRT), Liquid Crystal Display (LCD), or the like. The main display 80 or the sub display 81 may be coupled with or separated from the main body 2.

The ultrasonic imaging apparatus 1 may further include a moving unit 9. The moving unit 9 may connect the display unit 8 to the main body 2. The moving unit 9 may be configured to move the display unit 8 with respect to the main body 2. The moving unit 9 enables the display unit 8 to be located spaced from the main body 2. The moving unit 9 will be described in detail, later.

The main body 2 may include the input unit 7. The input unit 7 may be implemented as a keyboard, one or more buttons, a dial, a foot switch, or a foot pedal. If the input unit 7 is a keyboard, the input unit 7 may be mounted on the upper part of the main body 2. If the input unit 7 is a foot switch or a foot pedal, the input unit 7 may be provided in the lower part of the main body 2. A sonographer may use the input unit 7 to control operations of the ultrasonic imaging apparatus 1.

The input unit 7 may be implemented as an input panel 70 on which a keyboard, one or more buttons, a dial, and the like are arranged. The input panel 70 may be mounted on the main body 2. At one side of the input panel 70, a handle part 71 may be provided. A user may hold the handle part 71 and apply a force to move the ultrasonic imaging apparatus 1.

The ultrasound probe 3 may connect to the main body 2 through a connecting member 5. The connecting member 5 may include a cable 50 and a connector 51. The ultrasound probe 3 may be connected to one end of the cable 50, and the other end of the cable 50 may be connected to a male connector 51. The male connector 51 may be detachably inserted into a female connector 20 formed in the main body 2 so as to connect the ultrasound probe 3 to the main body 2.

One or more probe holders 4 for accommodating the ultrasound probe 3 may be provided at one lateral side of the ultrasonic imaging apparatus 1. The sonographer may put the ultrasound probe 4 into one of the probe holders 4 to safely keep the ultrasound probe 3 when he/she does not use the ultrasonic imaging apparatus 1. For example, each probe holder 4 may be formed in the input panel 70 in the form of a hole through which a handle part of the ultrasound probe 3 can pass. The ultrasound probe 3 may be inserted into the hole formed in the input panel 70 to thereby be safely kept. As another example, the probe holder 4 may be provided in the shape of a holder attached to the main body 2. The ultrasound probe 3 may be inserted into and rested in the holder 4.

At the front and back parts of the main body 2, handle parts 21 and 71 may be provided so that a user can hold the handle parts 21 and 71 to move the ultrasonic imaging apparatus 1. The handle parts 21 and 71 may include a first handle part 71 provided at the front part of the main body 2, and a second handle part 21 provided at the back part of the main body 2. The first handle part 71 may be provided at one side of the input panel 7, and the second handle part 21 may be provided with a protruding structure at the back part of the main body 2.

The main body 2 may include a plurality of castors 22 and 23 to move the ultrasonic imaging apparatus 1. The castors 22 and 23 may be aligned to move the main body 2 in a specific direction (an alignment movement mode), may move the main body freely (a free movement mode), or may be locked to fix the main body 2 at a specific location (a locking mode).

The castors 22 and 23 may include first castors 22 and second castors 23. If a direction in which the input unit 7 and the display unit 8 are located is the front, and a direction that is opposite to the front is the back, the first castors 22 may be located in the front of the main body 2, and the second castors 23 may be located in the back of the main body 2. The first castors 22 may be located at both left and right sides in the front of the main body 2, and the second castors 23 may be located at both left and right sides in the back of the main body 2 in correspondence to the first castors 22.

The main body 2 may include a manipulating unit 25 to control the castors 22 and 23. The manipulating unit 25 may be provided in the form of a foot pedal, as shown in FIG. 1, or in the form of a button or dial. The user may press down the foot pedal 25 and hold the first handle part 71 to move or stop the ultrasonic imaging apparatus 1.

Hereinafter, the moving unit 9 according to an embodiment of the present disclosure will be described in detail.

Figure 2:
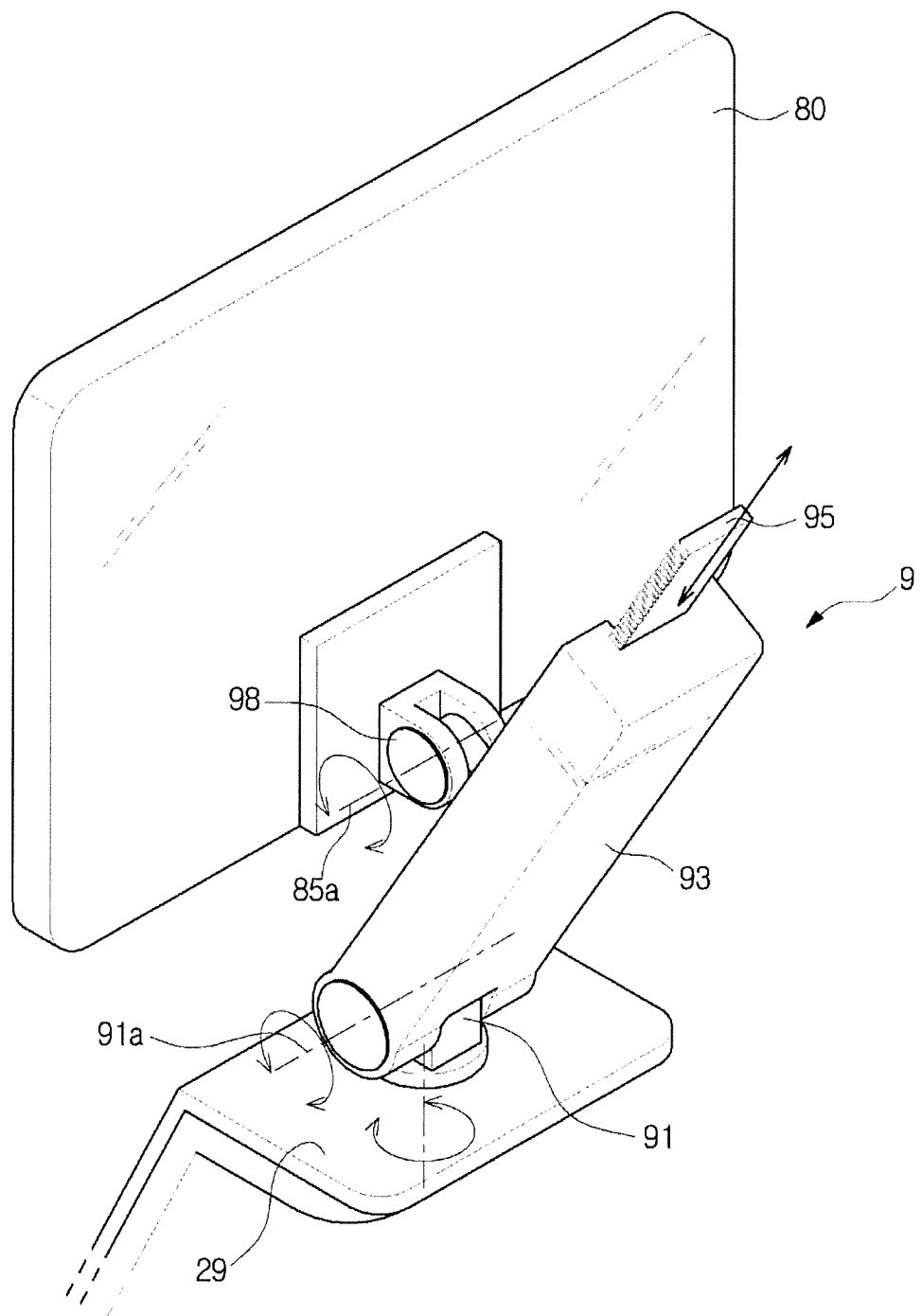
FIG. 2 shows a moving member installed in a rotating arm, according to an embodiment of the present disclosure, and the back part of a display unit coupled with a moving unit including the moving member.
Figure 3:
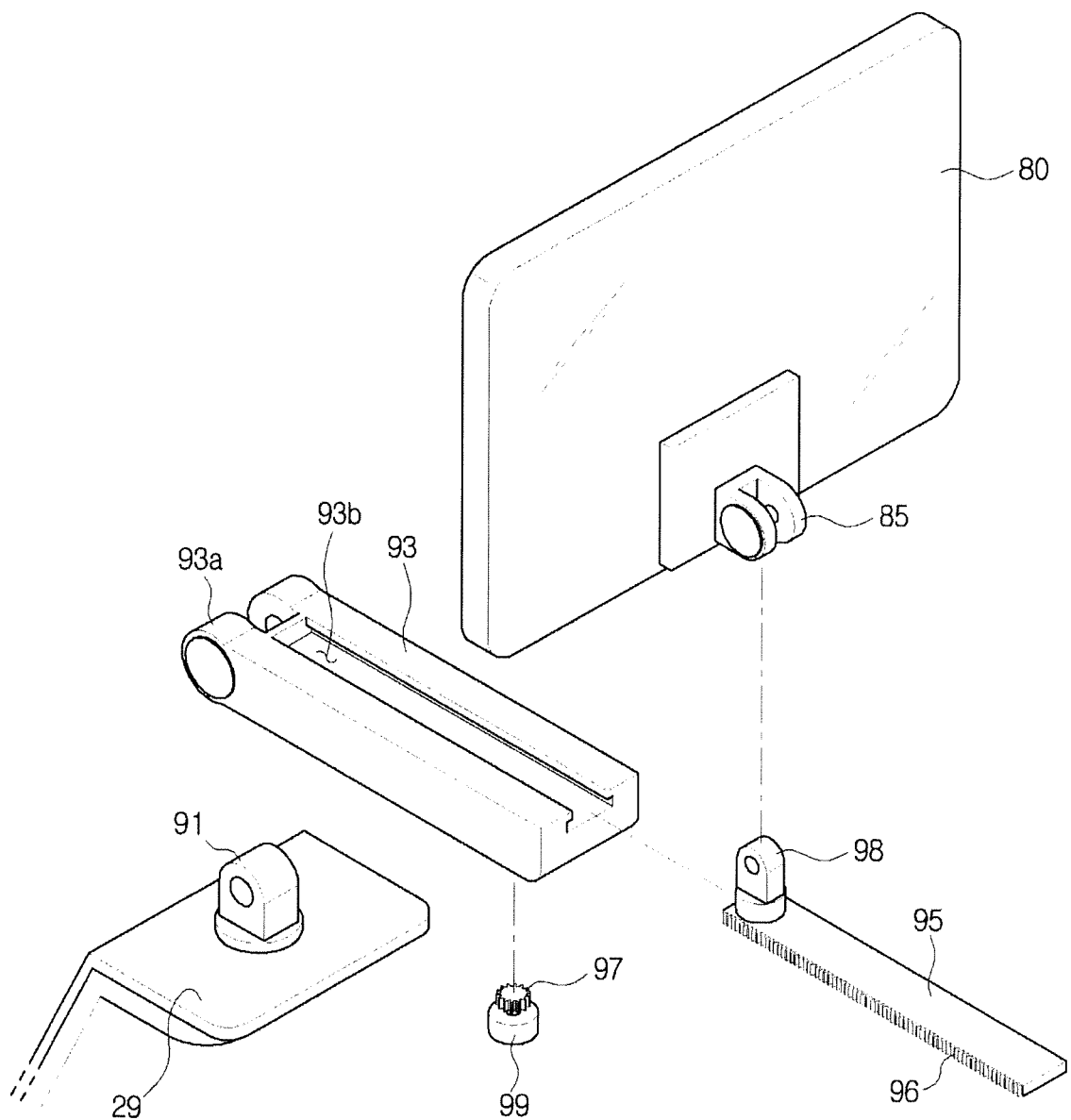
FIG. 3 is an exploded perspective view showing a configuration of the moving unit of FIG. 2.
Figure 4:
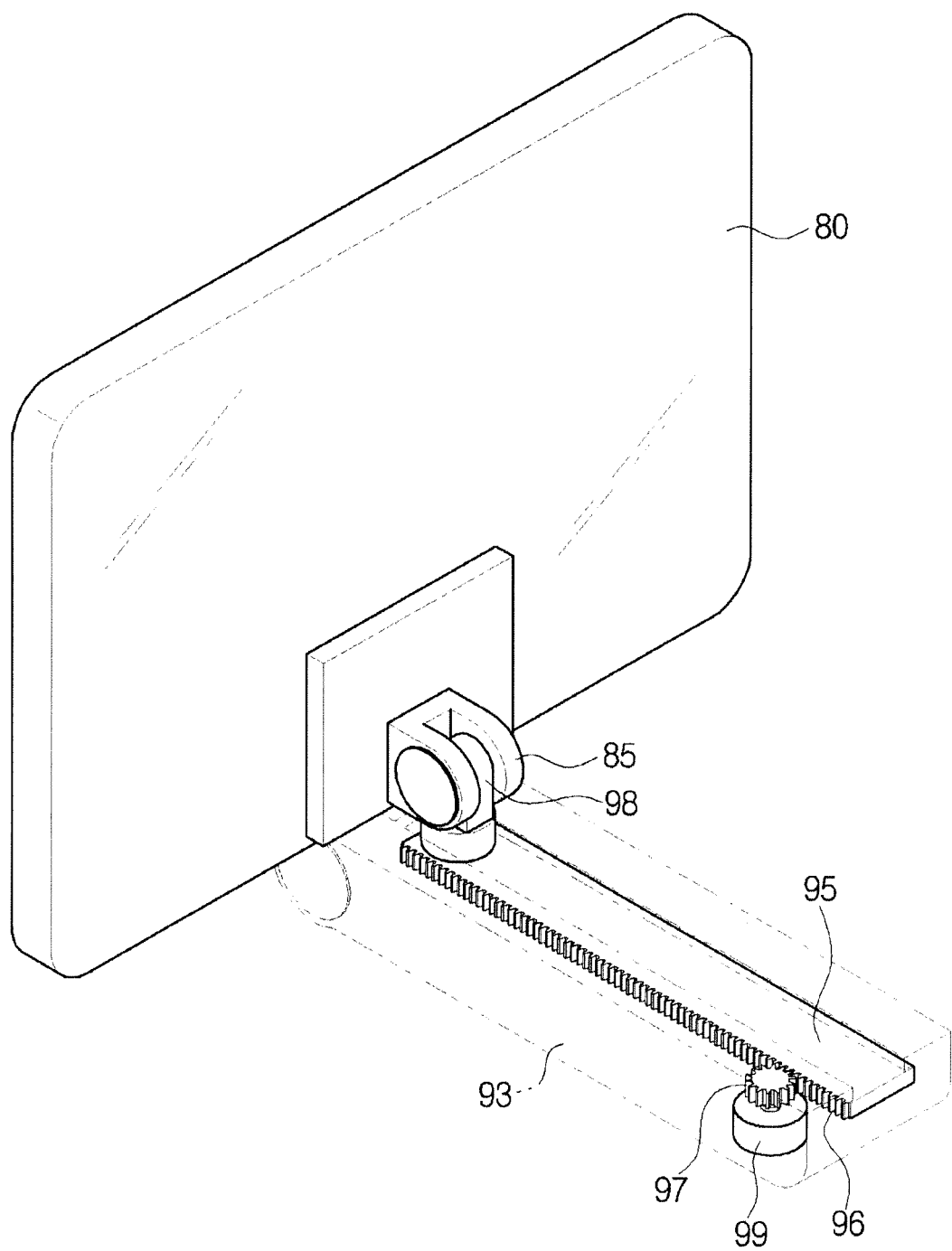
FIG. 4 is a back view of the moving unit including the moving member of FIG. 2 coupled with the rotating arm.
Figure 5:
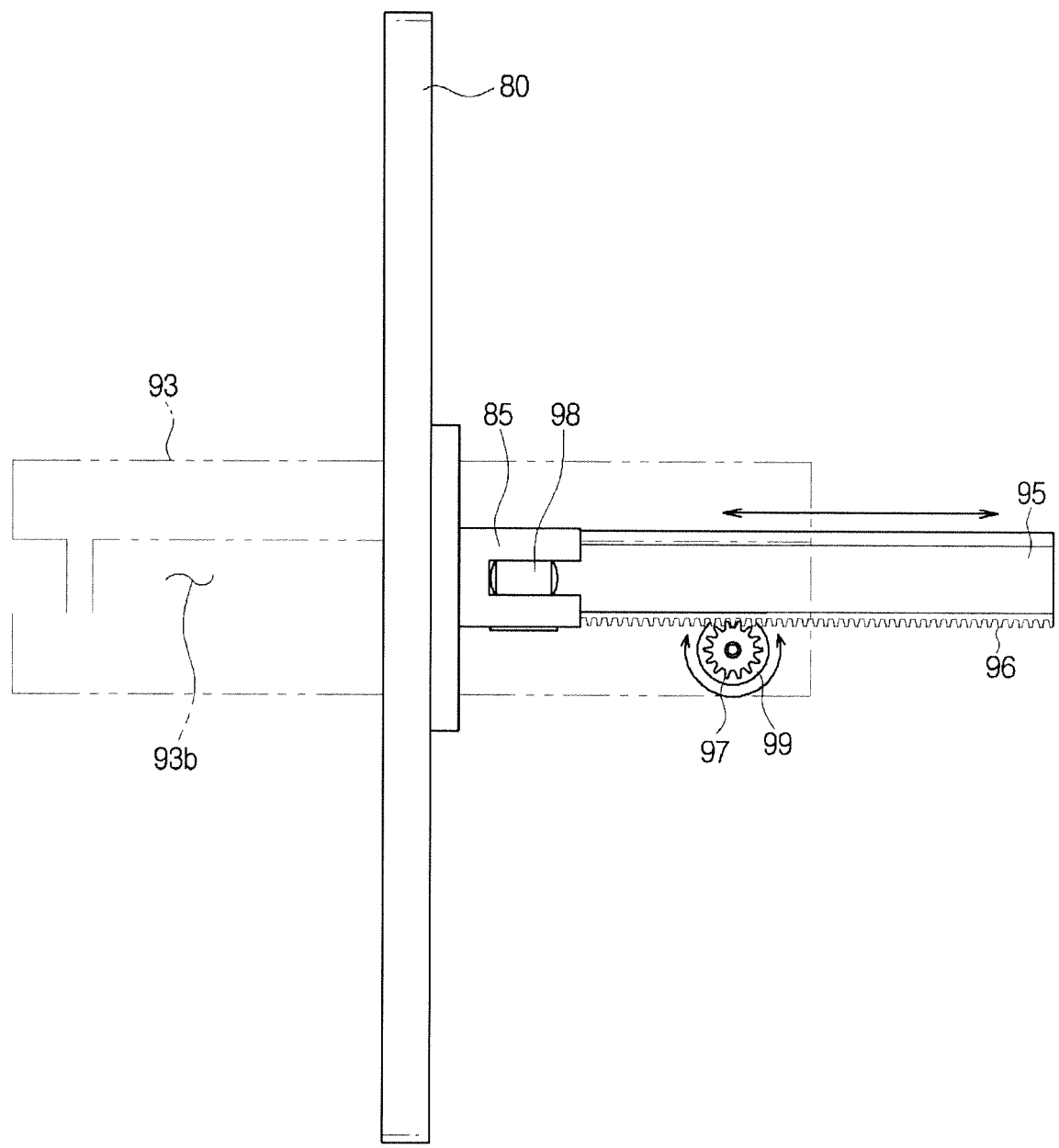
FIG. 5 is a top view of the moving unit of FIG. 4.
Figure 6:
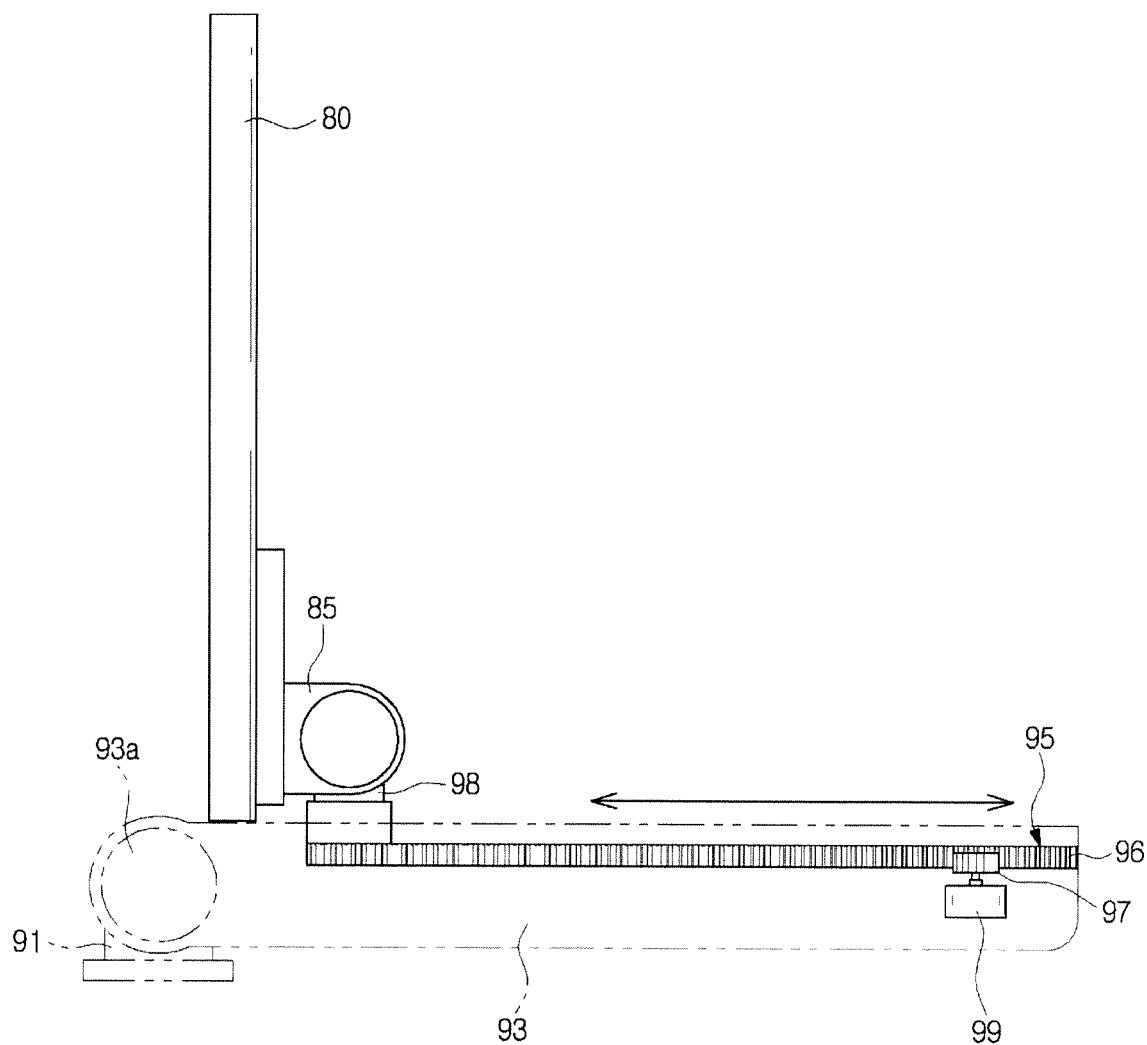
FIG. 6 is a side view of the moving unit of FIG. 4.

FIG. 2 shows a moving member installed in a rotating arm, according to an embodiment of the present disclosure, and the back part of a display unit coupled with a moving unit including the moving member, FIG. 3 is an exploded perspective view showing a configuration of the moving unit of FIG. 2, FIG. 4 is a back view of the moving unit including the moving member of FIG. 2 coupled with the rotating arm, FIG. 5 is a top view of the moving unit of FIG. 4, and FIG. 6 is a side view of the moving unit of FIG. 4.

Referring to FIGS. 1 to 6, the moving unit 9 may connect the display unit 8 to the main body 2. The moving unit 9 may be configured to move the display unit 8 with respect to the main body 2. The moving unit 9 may include a first coupling member 91, a rotating arm 93, and a moving member 95. Hereinafter, for convenience of description, the display unit 8 is assumed to be the main display 80, however, the moving unit 9 may be applied to both the main display 80 and the sub display 81.

One end of the rotating arm 93 may be coupled with the main body 2. The rotating arm 93 may be rotatably coupled with a part of the main body 2. The other end of the rotating arm 93 may be coupled with the display unit 8 so that the rotating arm 93 can rotate together with the display unit 8.

The rotating arm 93 may be coupled with the first coupling member 91 attached on a part of the main body 2. The rotating arm 93 may be rotatably coupled with the first coupling member 91 such that the rotating arm 93 can rotate with respect to a rotating axis 91*a*. At one end of the rotating arm 93, a rotating arm coupling part 93*a* that is coupled with the first coupling member 91 may be formed. The rotating arm coupling part 93*a* may be coupled with the first coupling member 91 so that the rotating arm 93 can rotate with respect to the rotating arm rotating axis 91*a*.

The first coupling member 91 may be disposed on the upper part of the main body 2. The main body 2 may further include a supporting member 29 coupled with the upper part of the main body 2, and bent upward. The first coupling member 91 may be attached on the supporting member 29, and spaced upward from the upper surface of the main body 2.

As shown in FIG. 2, the first coupling member 91 can rotate. The first coupling member 91 may be rotatable on a first plane, wherein the first plane may be defined as a plane that is parallel to the upper surface of the main body 2. That is, the first coupling member 91 may be rotatable on a first plane that is parallel to the supporting member 29. When the first coupling member 91 rotates, the rotating arm 93 may rotate together with the first coupling member 91.

When the first coupling member 91 rotates, the rotating arm 93 may rotate and move on the first plane together with the first coupling member 91. Also, the rotating arm 93 may rotate with respect to the rotating axis 91*a*, more specifically, the rotating arm 93 may rotate with respect to the rotating axis 91*a* on a second plane that is vertical to the first plane. The rotating arm 93 may rotate and move on the first plane, may rotate and move on the second plane, or may rotate and move on both the first plane and the second plane.

The moving member 95 may be installed in the rotating arm 93. The moving member 95 may move along the rotating arm 93. More specifically, the moving member 95 may slide in both directions along the rotating arm 93.

One end of the moving member 95 may be coupled with the display unit 8. The moving member 95 may move along the rotating arm 93, together with the display unit 8. The moving member 95 may be inserted into a moving groove 93*b* formed in the rotating arm 93 to thus be coupled with the rotating arm 93. The moving member 95 may move along the moving groove 93*b* in the longitudinal direction of the rotating arm 93.

According to an embodiment of the present disclosure, the moving unit 9 may further include a rack gear 96 formed at one lateral side of the moving member 95, a pinion gear 97 interlocked with the rack gear 96, and a second coupling member 98 coupled with the display unit 8.

As shown in FIGS. 4 to 6, the rack gear 96 and the pinion gear 97 may enable the moving member 95 to move along the rotating arm 93. The rack gear 96 may be formed at one lateral side of the moving member 95, and the pinion gear 97 may be installed in the rotating arm 93 and interlocked with the rack gear 96. The pinion gear 97 may be configured to restrict movement of the moving member 95 with the rack gear 96 within a predetermined range. The pinion gear 97 may be configured to fix the display unit 8 and the moving member 95 at a position to which the display unit 8 moves.

The moving unit 9 may further include a driving member 99 coupled with the pinion gear 97. The driving member 99 may generate a rotating force for rotating the pinion gear 97. If a user manipulates the input unit 7 in order to adjust a position of the display unit 8, the driving member 99 may rotate the pinion gear 97 according to the user's manipulation to move the display member 8.

The second coupling member 98 may be disposed on one end of the moving member 95. The second coupling member 98 may be coupled with the display unit 8 so that the display unit 8 can move together with the moving member 95. The second coupling member 98 may be coupled with a display coupling member 85 attached on the back surface of the display unit 8. As shown in FIG. 2, the second coupling member 98 may enable the display unit 8 to rotate with respect to a display rotating axis 85*a* of the second coupling member 98. Accordingly, the display unit 8 may rotate with respect to the display rotating axis 85*a*.

Figure 7:
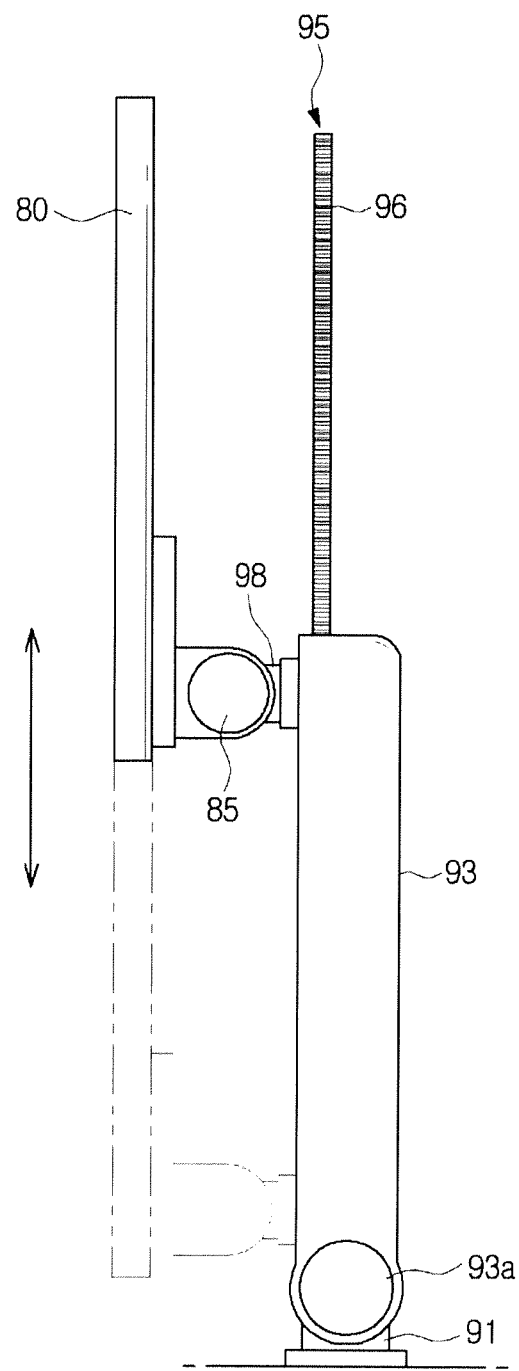
FIGS. 7 to 9 show movements of the display unit of FIG. 2 according to driving of a rotating arm.
Figure 8:
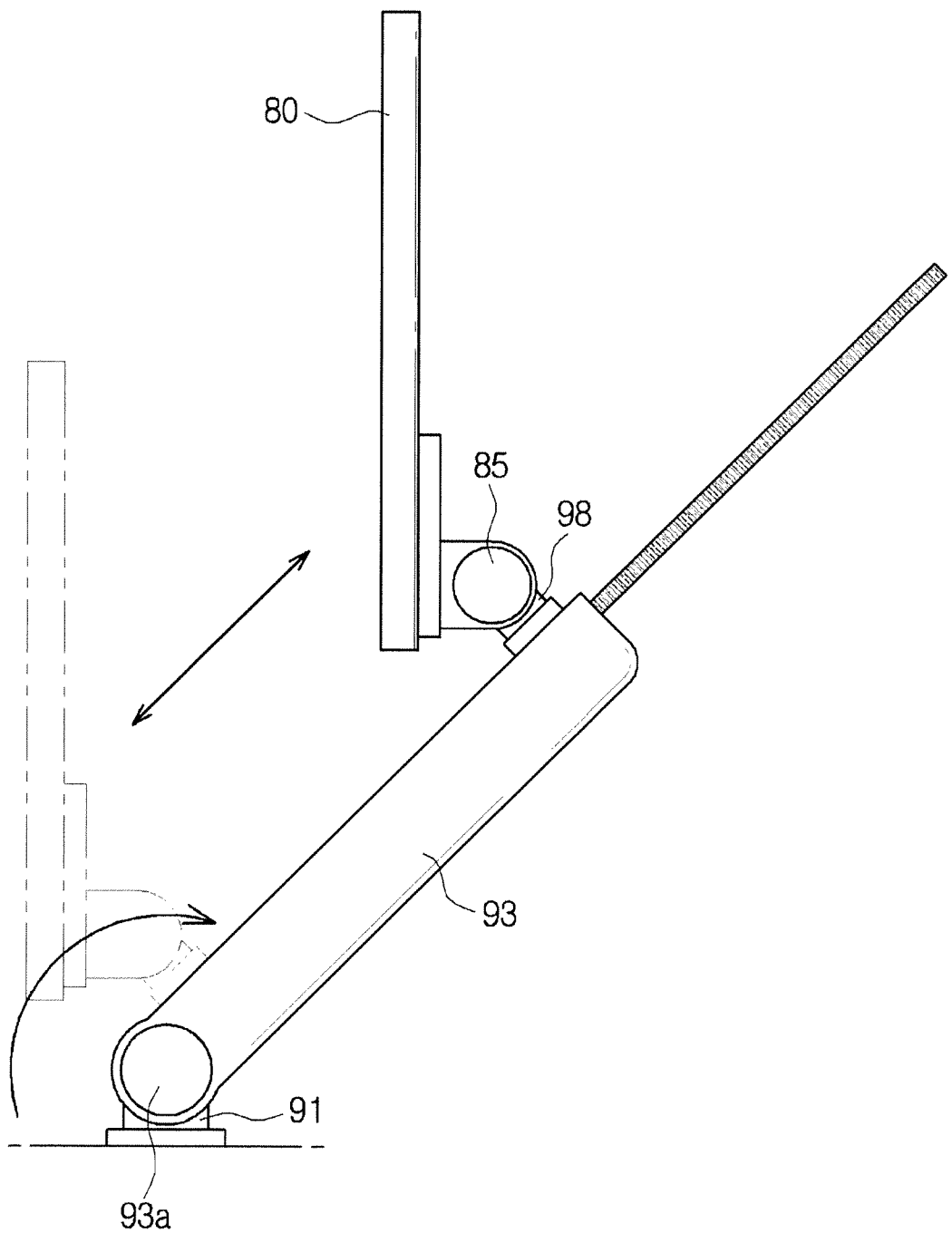
Figure 9:
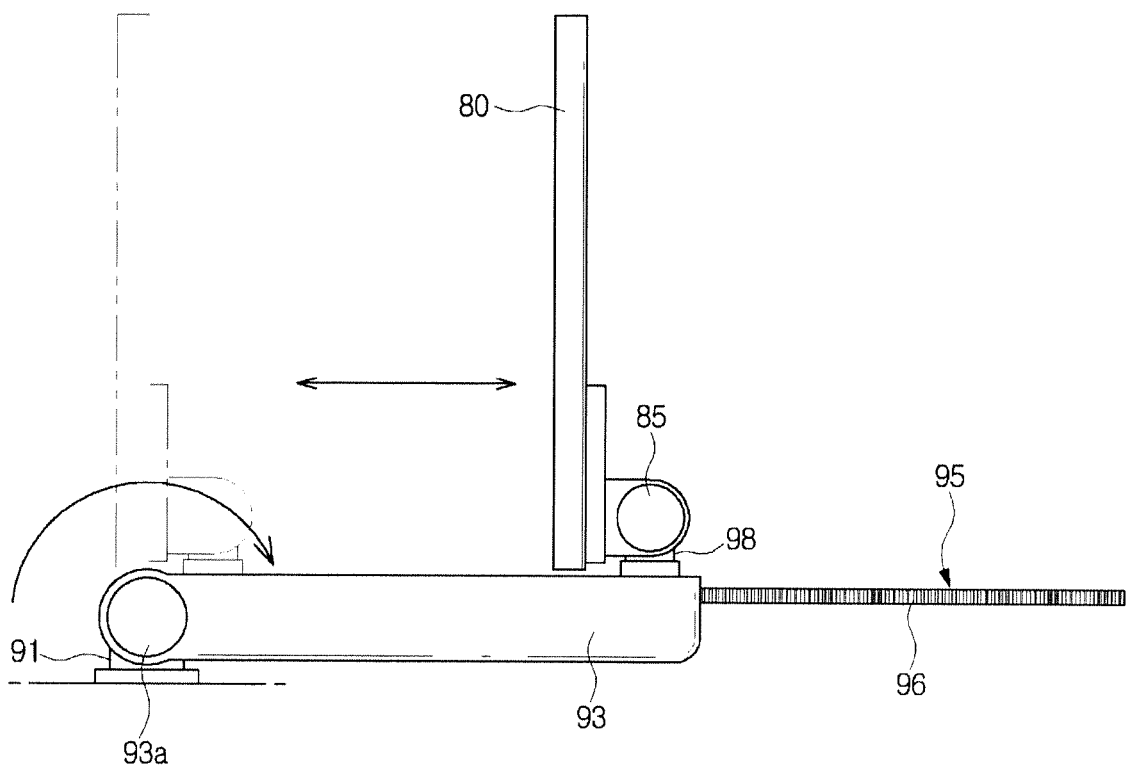

FIGS. 7 to 9 show movements of the display unit 8 of FIG. 2 according to driving of a rotating arm.

As shown in FIGS. 7 to 9, the rotating arm 93 may rotate with respect to the first coupling member 91. FIG. 7 shows a state when the rotating arm 93 is positioned vertically with respect to the main body 2 (see FIG. 1), FIG. 8 shows a state when the rotating arm 93 rotates at a predetermined angle backward with respect to the main body 2, and FIG. 9 shows a state when the rotating arm 93 rotates backward with respect to the main body 2 to be at a position that is parallel to the main body 2. That is, the rotating arm 93 may rotate backward with respect to the main body 2, from a position at which the rotating arm 93 is vertical to the main body 2, as shown in FIG. 7, to a position at which the rotating arm 93 is parallel to the main body 2, as shown in FIG. 9. On the contrary, the rotating arm 93 may rotate from the position at which the rotating arm 93 is parallel to the main body 2, as shown in FIG. 9, to the position at which the rotating arm 93 is vertical to the main body 2, as shown in FIG. 7. The rotating arm 93 may rotate in both directions with respect to the first coupling member 91. Accordingly, the display unit 8 may rotate in both directions with respect to the first coupling member 91, together with the rotating arm 93.

The display unit 8 may move along the rotating arm 93. The display unit 8 may move back and forth in the longitudinal direction of the rotating arm 93, together with the moving member 95. The display unit 8 can move in the longitudinal direction of the rotating arm 93 even when the rotating arm 93 is at different positions, as shown in FIGS. 7 to 9. Accordingly, the display unit 8 may rotate in both directions with respect to the first coupling member 91, together with the rotating arm 93, and independently slide along the rotating arm 93 in the longitudinal direction of the rotating arm 93.

Also, as shown in FIG. 2, since the first coupling member 91 is rotatable with respect to the main body 2, the display unit 8 may rotate together with the first coupling member 91. As described above, according to an embodiment of the present disclosure, the display unit 8 may be easily moved to various positions by the moving unit 9.

Hereinafter, an ultrasonic imaging apparatus 1 including a moving unit according to another embodiment of the present disclosure will be described. In the ultrasonic imaging apparatus 1 according to the current embodiment, the configuration of a moving unit is different from that of the moving unit 100 included in the ultrasonic imaging apparatus 1 of FIG. 2, and the remaining components are the same as the corresponding ones of the ultrasonic imaging apparatus 1 of FIG. 2. Accordingly, descriptions about the same components will be omitted.

Figure 10:
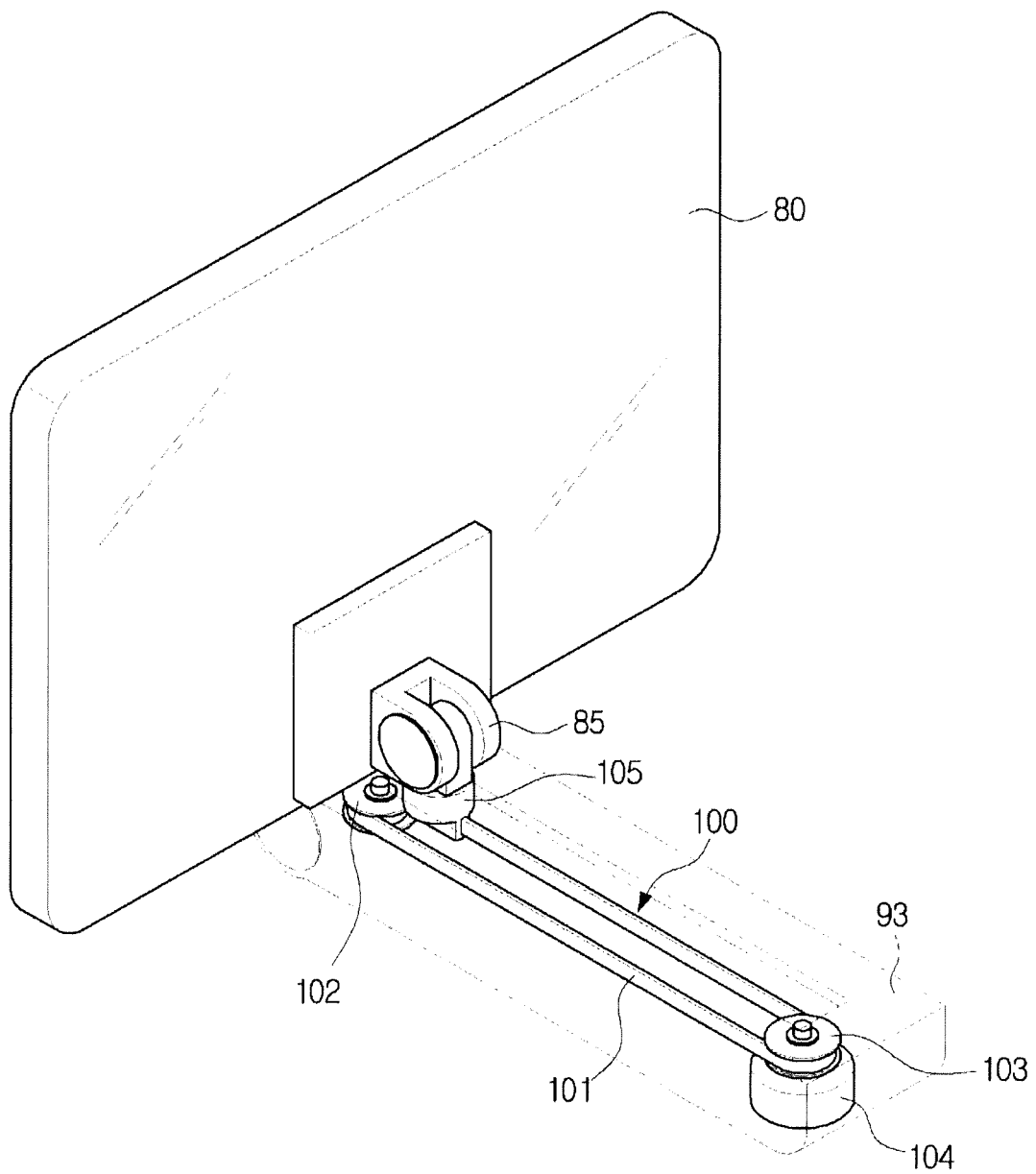
FIG. 10 shows a moving unit according to another embodiment of the present disclosure, coupled with a display unit and including a belt member installed in a rotating arm.
Figure 11:
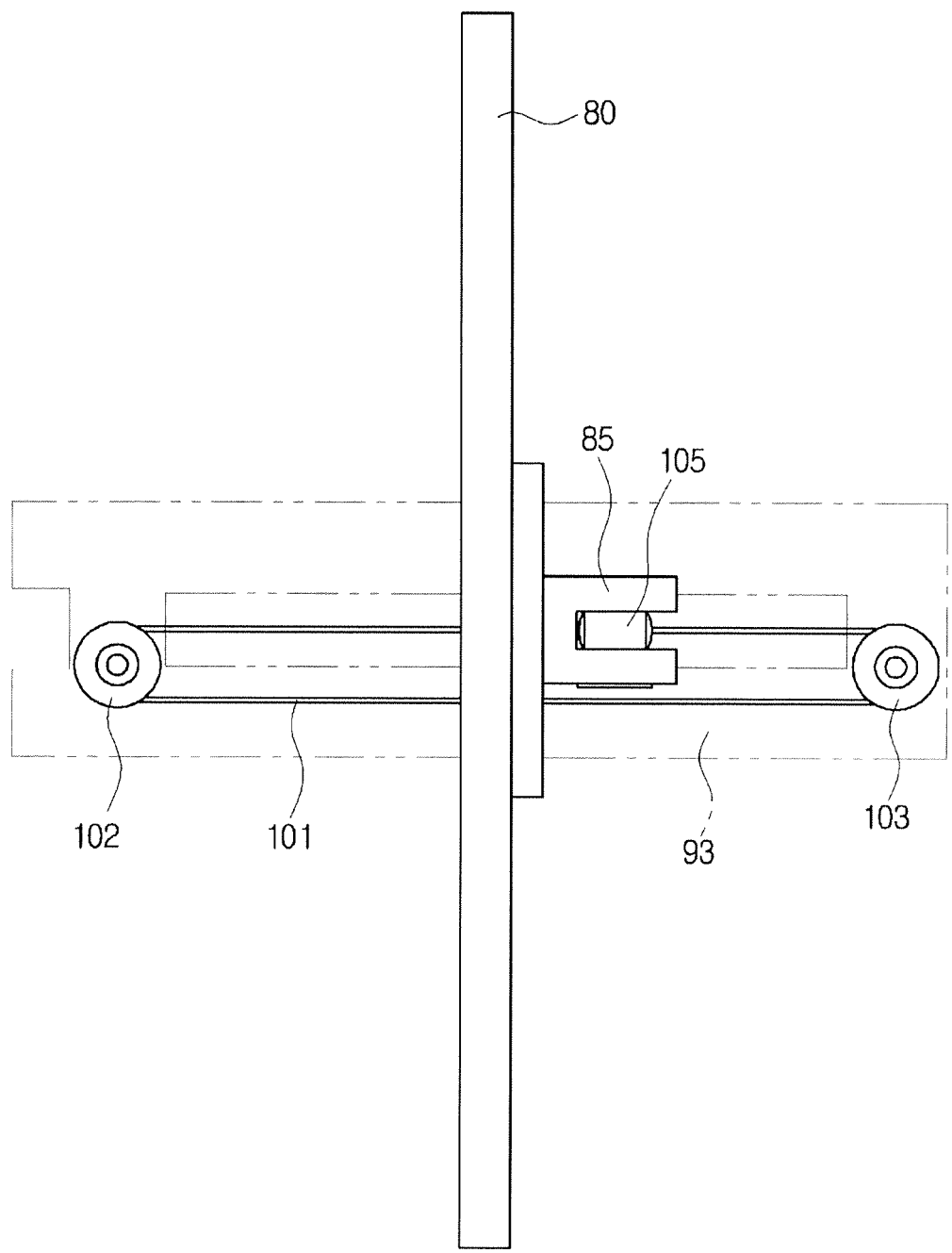
FIG. 11 is a top view of the moving unit of FIG. 10.
Figure 12:
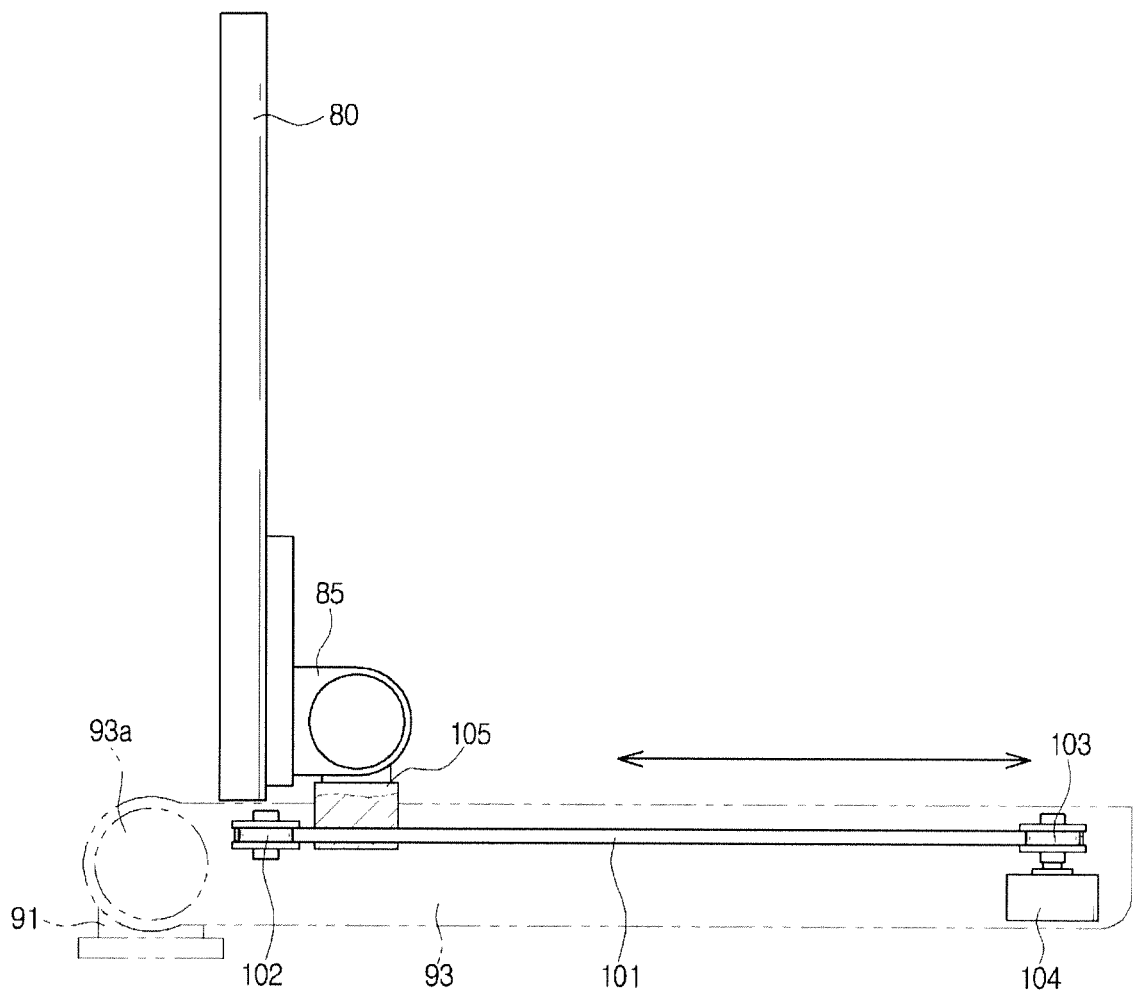
FIG. 12 is a side view of the moving unit of FIG. 10.

FIG. 10 shows a moving unit according to another embodiment of the present disclosure, coupled with a display unit and including a belt member installed in a rotating arm, FIG. 11 is a top view of the moving unit of FIG. 10, and FIG. 12 is a side view of the moving unit of FIG. 10.

Referring to FIGS. 10 to 12, a moving unit 100 may include a first coupling member 91, a rotating arm 93, a belt member 101, pulley members 102 and 103, and a second coupling member 105.

The belt member 101 and the pulley members 102 and 103 may be installed in the rotating arm 93. The pulley members 102 and 103 may include a first pulley 102 and a second pulley 103. For example, the first pulley 102 may be disposed at a location close to the first coupling member 91 in the rotating arm 93, and the second pulley 103 may be disposed at a location that is opposite to the first coupling member 91 in the rotating arm 93. The belt member 101 may be disposed to surround the first pulley 102 and the second pulley 103, and move according to rotation of the first pulley 101 and the second pulley 103. The belt member 101 may move in both directions along the longitudinal direction of the rotating arm 93, according to rotation directions of the first pulley 102 and the second pulley 103.

The second coupling member 105 may be coupled with a part of the belt member 101. The second coupling member 105 may be coupled with the display unit 8 to move along the belt member 101 together with the display unit 8. Accordingly, the display unit 8 may move in the longitudinal direction of the rotating arm 93 according to the movement direction of the belt member 101. Also, the second coupling member 105 may enable the display unit 8 to rotate with respect to the second coupling member 105.

The moving unit 100 may further include a belt driver 104. The belt driver 104 may generate a rotating force to move the belt member 101. Accordingly, if a user manipulates the input unit 7 in order to adjust a position of the display unit 8, the belt driver 104 may move the belt member 101 to move the display unit 8.

Hereinafter, an ultrasonic imaging apparatus 1 including a moving unit according to still another embodiment of the present disclosure will be described. In the ultrasonic imaging apparatus 1 according to the current embodiment, the configuration of a moving unit is different from that of the moving unit 100 included in the ultrasonic imaging apparatus 1 of FIG. 2, and the remaining components are the same as the corresponding ones of the ultrasonic imaging apparatus 1 of FIG. 2. Accordingly, descriptions about the same components will be omitted.

Figure 13:
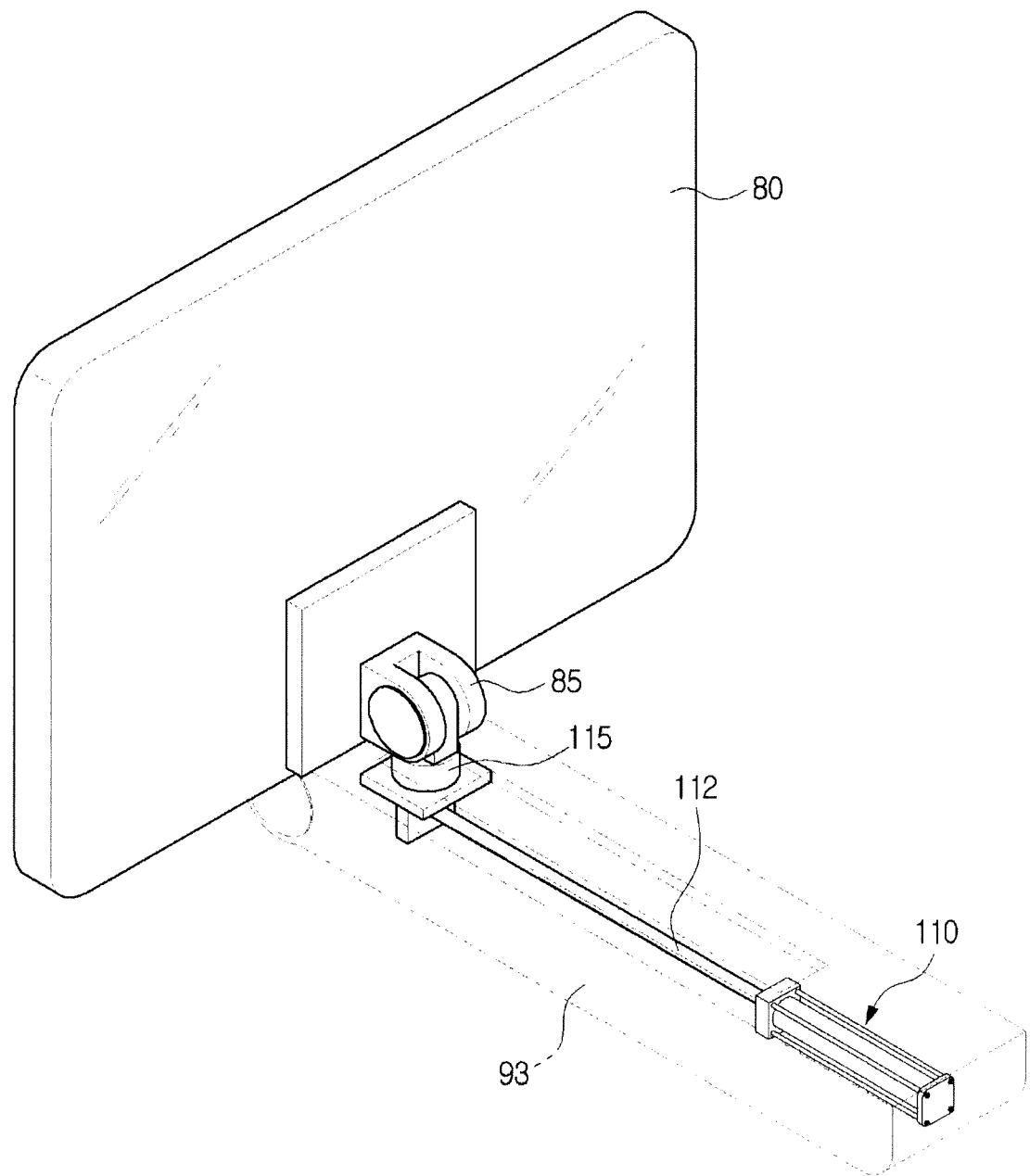
FIG. 13 shows a moving unit according to still another embodiment of the present disclosure, coupled with a display unit and including a cylinder and a plunger installed in a rotating arm.
Figure 14:
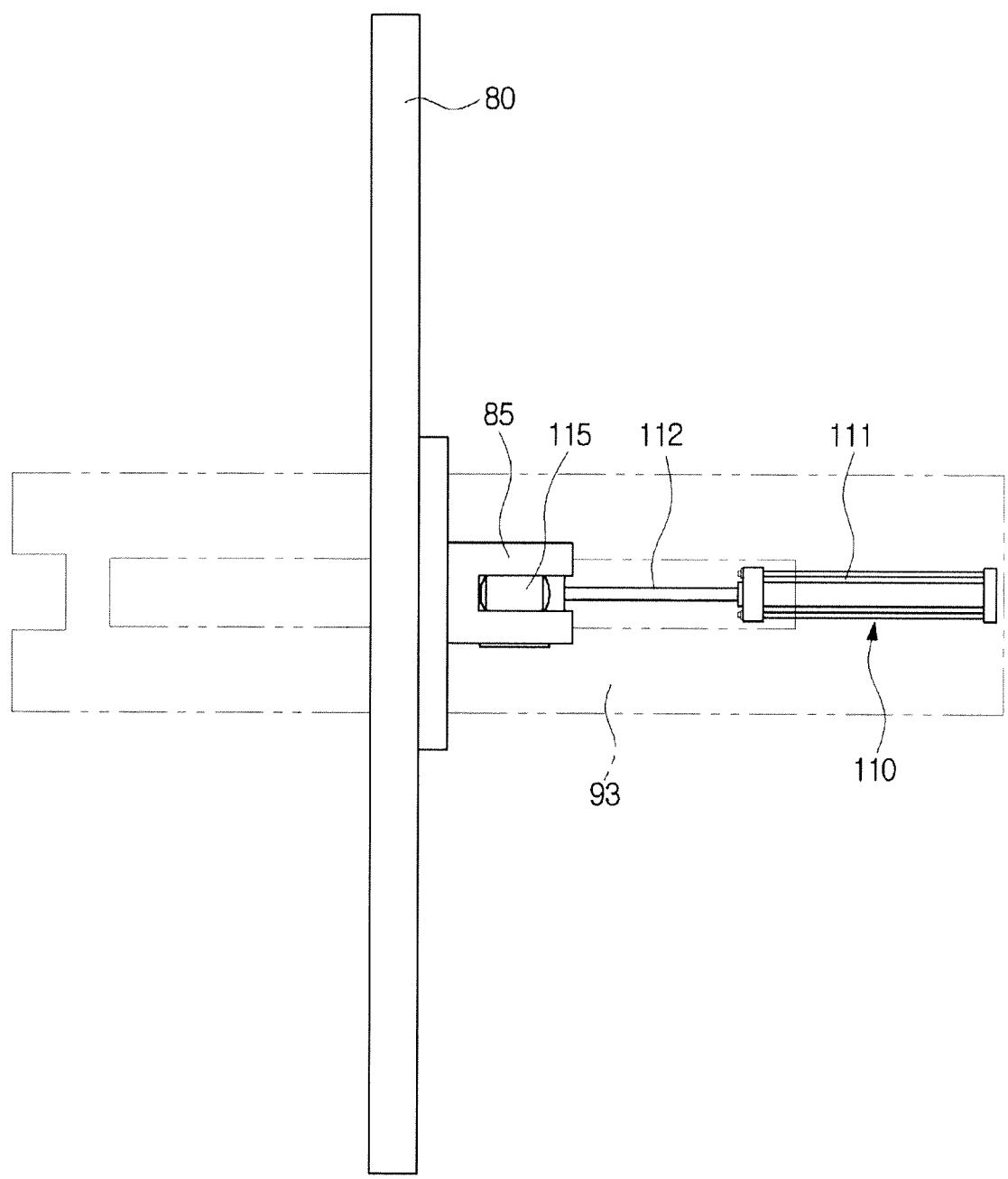
FIG. 14 is a top view of the moving unit of FIG. 13.
Figure 15:
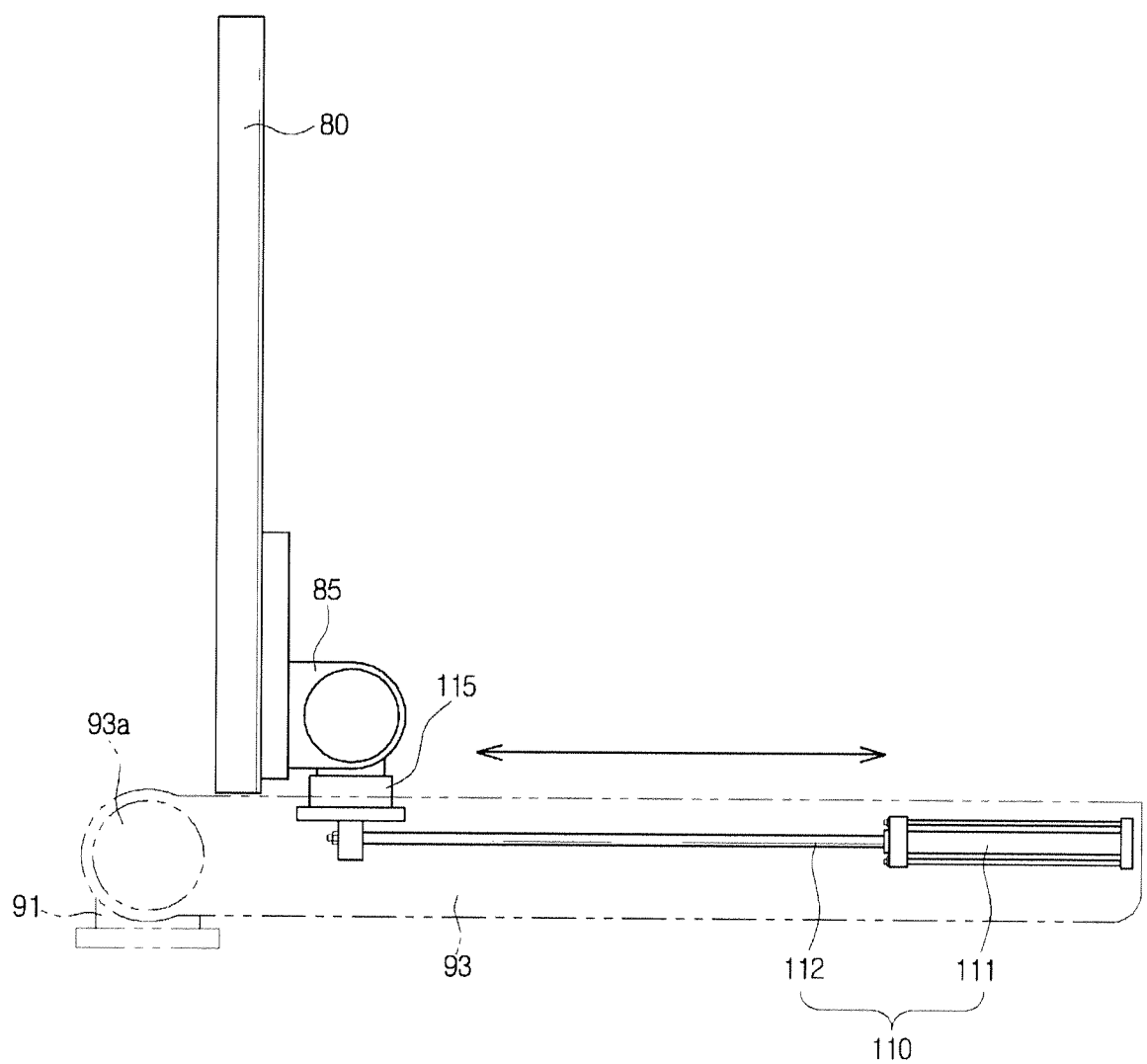
FIG. 15 is a side view of the moving unit of FIG. 13.

FIG. 13 shows a moving unit according to still another embodiment of the present disclosure, coupled with the display unit 8 and including a cylinder and a plunger installed in the rotating arm 93, FIG. 14 is a top view of the moving unit of FIG. 13, and FIG. 15 is a side view of the moving unit of FIG. 13.

Referring to FIGS. 13 to 15, a moving unit 110 may include a first coupling member 91, a rotating arm 93, a cylinder 111, a plunger 112, and a second coupling member 115.

The cylinder 111 and the plunger 112 may be installed in the rotating arm 93. The cylinder 111 may be installed at one end of the rotating arm 93, and the plunger 112 may be connected to the cylinder 111 to move back and forth in the longitudinal direction of the rotating arm 93 by oil pressure of the cylinder 111.

The second coupling member 115 may be coupled with one end of the plunger 112. The second coupling member 115 may be coupled with the display unit 8, and move along the plunger 112 together with the display unit 8. Accordingly, the display unit 8 may move in the longitudinal direction of the rotating arm 93 according to the movement direction of the plunger 112. Also, the second coupling unit 115 may enable the display unit 8 to rotate with respect to the second coupling member 115.

According to the embodiments of the present disclosure, the display unit of the ultrasonic imaging apparatus can be easily moved.

More specifically, the display unit of the ultrasonic imaging apparatus may be easily moved in front, back, left, and right directions by the moving unit.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. An ultrasonic imaging apparatus comprising:
   a main body;
   a probe configured to irradiate ultrasonic waves and to receive ultrasonic waves, and connected to the main body to transmit an ultrasonic signal corresponding to the received ultrasonic waves to the main body;
   a display unit connected to the main body in such a manner to be movable with respect to the main body; and
   a moving unit configured to connect the display unit to the main body, and to enable the display unit to move with respect to the main body,
   wherein the moving unit comprises:
      a first coupling member rotatably attached on a part of the main body;
      a second coupling member to which the display unit is rotatably coupled;
      a rotating arm coupled with the first coupling member and configured to rotate with respect to the first coupling member; and
      a moving member having the second coupling member disposed at one end of the moving member, and installed in the rotating arm to enable the display unit to move in a longitudinal direction of the rotating arm, wherein the second coupling member is configured to move within the rotating arm, wherein the first coupling member is configured to be rotatable on a first plane, wherein the rotating arm is configured to rotate together with the first coupling member, and wherein the rotating arm is configured to be rotatable on a second plane that is vertical to the first plane.

2. The ultrasonic imaging apparatus according to claim 1, wherein the moving unit further comprises a rack gear and a pinion gear, and one of the rack gear and the pinion gear moves back and forth in the longitudinal direction of the rotating arm.

3. The ultrasonic imaging apparatus according to claim 1, wherein the moving unit further comprises a belt member configured to move in both directions along the longitudinal direction of the rotating arm, and the second coupling member is coupled with a part of the belt member and configured to move together with the belt member.

4. The ultrasonic imaging apparatus according to claim 1, wherein the moving, unit further comprises a hydraulic cylinder configured to move back and forth along, the longitudinal direction of the rotating arm, and the second coupling member is coupled with one end of the hydraulic cylinder and configured to move together with the hydraulic cylinder.

* * * * *